United States Patent
Teramae et al.

(10) Patent No.: US 11,141,247 B2
(45) Date of Patent: Oct. 12, 2021

(54) BLOCK-LIKE COMPOSITE MATERIAL FOR DENTAL CUTTING AND PROCESSING HAVING MULTILAYERED STRUCTURE INCLUDING LAYERS WITH DIFFERENT TRANSPARENCIES AND CONTAINING FIBER MATERIAL

(71) Applicant: SHOFU INC., Kyoto (JP)

(72) Inventors: Mitsuji Teramae, Kyoto (JP); Masanori Goto, Kyoto (JP)

(73) Assignee: SHOFU INC., Kyoto (JP)

( * ) Notice: Subject to any disclaimer, the term of this patent is extended or adjusted under 35 U.S.C. 154(b) by 0 days.

(21) Appl. No.: 15/178,644

(22) Filed: Jun. 10, 2016

(65) Prior Publication Data
US 2017/0196667 A1    Jul. 13, 2017

(30) Foreign Application Priority Data
Jan. 13, 2016   (JP) .............................. JP2016-004229

(51) Int. Cl.
   B32B 7/02       (2019.01)
   A61C 13/08      (2006.01)
   A61K 6/16       (2020.01)
   A61K 6/887      (2020.01)
   A61C 13/00      (2006.01)
   A61C 13/087     (2006.01)
   A61C 13/09      (2006.01)

(52) U.S. Cl.
   CPC ........ *A61C 13/082* (2013.01); *A61C 13/0022* (2013.01); *A61C 13/087* (2013.01); *A61C 13/09* (2013.01); *A61K 6/16* (2020.01); *A61K 6/887* (2020.01)

(58) Field of Classification Search
None
See application file for complete search history.

(56) References Cited

U.S. PATENT DOCUMENTS

| | | |
|---|---|---|
| 5,098,304 A | 3/1992 | Scharf |
| 5,839,900 A | 11/1998 | Billet et al. |
| 6,039,569 A | 3/2000 | Prasad et al. |
| 6,114,409 A * | 9/2000 | Krebber .............. A61C 3/08 433/228.1 |
| 2009/0258965 A1 | 10/2009 | Lassila et al. |
| 2014/0099271 A1* | 4/2014 | Craig .............. A61K 6/083 424/52 |
| 2014/0206792 A1* | 7/2014 | Ishizaka ........... A61K 6/0005 523/115 |
| 2014/0295376 A1 | 10/2014 | Uchida et al. |
| 2015/0094396 A1* | 4/2015 | Nakatsuka ........ A61K 6/0005 523/116 |
| 2018/0028413 A1* | 2/2018 | Craig ............... A61K 6/0205 |

FOREIGN PATENT DOCUMENTS

| | | | |
|---|---|---|---|
| JP | 2004-500959 | 1/2004 | |
| JP | 5345054 | 11/2013 | |
| WO | 02/00135 | 1/2002 | |
| WO | 2009/154301 | 12/2009 | |
| WO | 2010/109496 | 9/2010 | |
| WO | WO 2015051095 A1 * | 4/2015 | ......... A61C 13/0004 |
| WO | WO 2015073365 A1 * | 5/2015 | ......... A61C 13/0004 |

OTHER PUBLICATIONS

"Glass Fiber Differences and Properties" webpage; archived Apr. 28, 2015 and accessed Aug. 18, 2017; https://web.archive.org/web/20150428054210/http://www.build-on-prince.com/glass-fiber.html.*
Notification of Reasons for Refusal dated Feb. 23, 2016 in Japanese Patent Application No. 2016-004229, with English-language translation.
Extended European Search Report dated Jun. 21, 2017 in European Patent Application No. 16173872.9.

* cited by examiner

*Primary Examiner* — Zachary M Davis
(74) *Attorney, Agent, or Firm* — Wenderoth, Lind & Ponack, L.L.P.

(57) ABSTRACT

The present invention relates to a composite material which can be used as a dental prosthesis device (crown, bridge), and specifically, relates to a composite material including a curable resin and a fiber material, and more specifically relates to a block-like composite material for dental cutting and processing characterized by having a multilayered structure including at least two layers having different transparencies. There are no technical information relating to a color tone and a transparency of the fiber material. To provide a block-like composite material for dental cutting and processing, wherein the block-like composite material has a multilayered structure including at least two layers having different transparencies, and the each layer includes a curable resin and a fiber material.

9 Claims, No Drawings

BLOCK-LIKE COMPOSITE MATERIAL FOR DENTAL CUTTING AND PROCESSING HAVING MULTILAYERED STRUCTURE INCLUDING LAYERS WITH DIFFERENT TRANSPARENCIES AND CONTAINING FIBER MATERIAL

BACKGROUND OF THE INVENTION

Field of the Invention

The present invention relates to a composite material which can be used as a dental prosthesis device (crown, bridge), and specifically, to a block-like composite material for dental cutting and processing, wherein the composite material comprises a curable resin and a fiber material, and has a multilayered structure including at least two layers having different transparencies.

Description of the Related Art

A composite material comprising a curable resin and a fiber material is widely used for a general industrial material as FRP (Fiber Reinforced Plastics). A big feature of FRP is to have strength equal to that of a metal material while being lighter than the metal material. FRP has been applied to a bridge frame material and a post material as the substitute material for a dental alloy which are used conventionally as a dental material. Selecting a fiber base composite material in a dental treatment is very effective from the view point of avoiding a risk of metallic allergy to the human body, not to speak of the view point of reduction of the weight of a prosthesis device.

As a conventional application example of a fiber base composite material in a dental field, Patent Literature 1: U.S. Pat. No. 5,098,304 discloses a dental prosthesis device (bridge) obtained by compositing a glass fiber material and a resin material. Patent Literature 2: U.S. Pat. No. 5,839,900 discloses a dental prosthesis device obtained by covering a frame of a glass fiber material with a composite resin and manufacturing method thereof. Patent Literature 3: U.S. Pat. No. 6,039,569 discloses a manufacturing method of a bridge frame by bridging between at least two abutment teeth using a fiber material. Patent Literature 4: WO 2010/109496 discloses a dental material obtained by overwrapping a sheet-like knitted fiber material and compositing the overwrapped fiber material and a polymerizable resin.

SUMMARY OF THE INVENTION

Technical Problem

Although all of prime aims of the prior arts disclosed in the above documents are a dental prosthesis treatment of a missing tooth, none of the above documents disclose technical information relating to a color tone and a transparency of a fiber material. Therefore, in the scope of the prior art disclosed in the above documents, it is impossible to prepare a dental prosthesis device which reproduces a complicated color tone and transparency which are derived from an enamel and a dentine included in a natural tooth.

An object of the present invention is to impart a distinct transparency to each layer of a layered structure formed of a composite material containing a fiber material, as in a natural tooth. A natural tooth has structurally a dentine and an enamel. The enamel consists mostly of an inorganic component (hydroxyapatite) and has a translucency. On the other hand, the dentin is a composite of an inorganic component (hydroxyapatite) and an organic component (collagen) and has a lower translucency than that of the enamel. Therefore, it is possible to impart an esthetic effect similar to that of a natural tooth by including both a portion having a transparency similar to that of an enamel and a portion having a transparency similar to that of a dentin in a composite material.

Solution to Problem

As a result of intensive studies in order to solve the above problem, it has been found by the present inventors that the problem is solved by using two or more curable resins or fiber materials having different refractive indexes in a composite material including a curable resin and a fiber material. Specifically, a layer where a difference between refractive indexes of a curable resin and a fiber material is large imparts a low transparency similar to that of a dentin and a layer where a difference between refractive indexes of a curable resin and a fiber material is small imparts a high transparency similar to that of an enamel. Also, both a layer corresponding to a dentin and a layer corresponding to an enamel may be disposed appropriately by forming a composite material into a block-like form which is capable of being cut and processed and by forming a composite material into a multilayered structure including at least two layers.

In the present invention, a transparency of a material may be expressed as contrast ratio. The contrast ratio in the present invention may be obtained by the values Y measured on a white background and on a black background for a material having the thickness adjusted at 1 mm. Specifically, the contrast ratio in the present invention may be obtained by the formula "the contrast ratio=$Y_B/Y_W$". In the formula, $Y_W$ is the value Y measured on a white background, and $Y_B$ is the value Y measured on a black background.

Among the existing dental materials, a porcelain (ceramic) and a hard resin are used as a material which reproduces the color tones of a dentin and an enamel by a layered structure. In a product using these materials, it has been found that a color tone and a transparency similar to those of a natural tooth are obtained by setting a contrast ratio of a material reproducing a color tone of a dentin to 0.55 or more, and by setting a contrast ration of a material representing a color tone of an enamel to less than 0.55 by many years' research.

Advantageous Effects of Invention

Since a block-like composite material for dental cutting and processing according to the present invention has a multilayered structure including at least two layers having different transparencies, and comprises a curable resin and a fiber material, the block-like composite material for dental cutting and processing according to the present invention makes it possible to manufacture a prosthesis device having high strength while having esthetics highly similar to natural teeth.

DETAILED DESCRIPTION OF THE PREFERRED EMBODIMENTS

The present invention provides:

(1) A block-like composite material for dental cutting and processing, wherein the block-like composite material has a multilayered structure including at least two layers having different transparencies, and the each layer includes a curable resin and a fiber material;

(2) The block-like composite material for dental cutting and processing according to (1), wherein, the block-like composite material includes two layers consisting of a highly transparent layer and a low transparent layer, a contrast ratio of the highly transparent layer is less than 0.55, and a contrast ratio of the low transparent layer is 0.55 or more;

(3) The block-like composite material for dental cutting and processing according to (1), wherein, the block-like composite material includes three layers consisting of a highly transparent layer, a middle transparency layer and a low transparent layer, a contrast ratio of the highly transparent layer is less than 0.50, a contrast ratio of the middle transparency layer is 0.50 or more and less than 0.60, and a contrast ratio of the low transparent layer is 0.60 or more; and (4) The block-like composite material for dental cutting and processing according to (1), wherein, the block-like composite material includes four or more layers consisting of a highly transparent layer, a middle transparency layer and a low transparent layer, a contrast ratio of the highly transparent layer is less than 0.50, a contrast ratio of the middle transparency layer is 0.50 or more and less than 0.60, a contrast ratio of the low transparent layer is 0.60 or more, each of the highly transparent layer, the middle transparency layer and the low transparent layer consists of a single layer or a plurality of layers having different transparencies, and a difference of contrast ratio between each layers is 0.02 or more.

A block-like composite material for dental cutting and processing according to the present invention has a multi-layered structure including at least two layers having different transparencies, and the each layer includes a curable resin and a fiber material. The components which can be used in the present invention are described below. A curable resin included in a block-like composite material according to the present invention may be obtained by polymerizing and curing a radical polymerizable monomer compound. Therefore, any radical polymerizable monomer compound may be used by polymerizing and curing. Among them, known radical polymerizable monomer compounds which are used as a dental material are preferably used. Specific examples of the radical polymerizable monomer compound may be monofunctional compounds including (meth)acrylic ester such as methyl (meth)acrylate, ethyl (meth)acrylate, n-butyl (meth)acrylate, isobutyl (meth)acrylate, tert-butyl (meth)acrylate, pentyl (meth)acrylate, isopentyl (meth)acrylate, neopentyl (meth)acrylate, glycidyl (meth)acrylate, tetrahydrofurfuryl (meth)acrylate, 2-hydroxyethyl (meth)acrylate, 2-hydroxypropyl (meth)acrylate, 3-chloro-2-hydroxypropyl (meth)acrylate, ethylene glycol acetoacetate (meth)acrylate, ethylene glycol mono(meth)acrylate, diethylene glycol mono(meth)acrylate, triethylene glycol mono(meth)acrylate, polyethylene glycol mono(meth)acrylate, methoxydiethylene glycol mono(meth)acrylate, methoxytetraethylene glycol (meth)acrylate, methoxypolyethylene glycol (meth)acrylate, β-(meth)acryloxyethyl hydrogen phthalate, β-(meth)acryloxyethyl hydrogen succinate, nonylphenoxyethyl (meth)acrylate, phenoxyethyl (meth)acrylate, phenoxydiethylene (meth)acrylate, N-(2-hydroxy-3-(meth)acryloyloxypropyl)-N-phenylglycine, N-(meth)acryloylglycine, 4-(meth)acryloyloxyethyl trimellitic anhydride; vinyl ester such as vinyl acetate and vinyl propionate; vinyl ether such as methyl vinyl ether, ethyl vinyl ether, isobutyl vinyl ether and (meth)acrylaldehyde ethyl acetal; alkenylbenzene such as styrene, vinyltoluene, α-methylstyrene and chlorostyrene; vinyl cyanide such as acrylonitrile and (meth)acrylonitrile; (meth)acrylaldehyde such as (meth)acrylaldehyde and 3-cyano(meth)acrylaldehyde; (meth)acrylic acid amide such as (meth)acrylamide, N-succin(meth)acrylamide and N,N-dimethyl(meth)acrylamide; (meth)acrylic acid such as (meth)acrylic acid, vinylacetic acid and crotonic acid, and a metal salt thereof; phosphate ester group-containing monomer compound such as acid phosphoethyl (meth)acrylate, acid phosphopropyl (meth)acrylate and 2-(meth)acryloyloxyethyl phenyl phosphoric acid, and a metal salt thereof; sulfonic acid group-containing monomer compound such as allylsulfonic acid, (meth)acrylic sulfonic acid, styrenesulfonic acid, and tert-butyl(meth)acrylamidesulfonic acid, and a metal salt thereof.

Specific examples of the radical polymerizable monomer compound may be bifunctional monomer compounds including dioldi(meth)acrylate such as of ethylenedioldi(meth)acrylate, propylenedioldi(meth)acrylate, propanedioldi(meth)acrylate, butanedioldi(meth)acrylate, hexanedioldi(meth)acrylate, octanedioldi(meth)acrylate, nonanedioldi(meth)acrylate, decanedioldi(meth)acrylate, and eicosanedioldi(meth)acrylate; ethylene glycol di(meth)acrylate, diethylene glycol di(meth)acrylate, triethylene glycol di(meth)acrylate, propylene glycol di(meth)acrylate, tetraethylene glycol di(meth)acrylate, polyethylene glycol di(meth)acrylate, 1,3-butylene glycol di(meth)acrylate, and neopentyl glycol di(meth)acrylate; a urethane monomer compound which is derived from an adduct of a vinyl monomer having a hydroxy group such as 2-hydroxyethyl (meth)acrylate, 2-hydroxypropyl (meth)acrylate or 3-chloro-2-hydroxypropyl (meth)acrylate, and a diisocyanate compound such as hexamethylene diisocyanate, trimethylhexamethylene diisocyanate, diisocyanate methylcyclohexane, isophorone diisocyanate or methyl bis(4-cyclohexyl isocyanate); a (meth)acrylate monomer compound having both an aromatic ring and a urethane bond which is derived from an adduct of a vinyl monomer having a hydroxy group such as 2-hydroxyethyl (meth)acrylate, 2-hydroxypropyl (meth)acrylate or 3-chloro-2-hydroxypropyl (meth)acrylate, and an aromatic group-containing diisocyanate compound such as diisocyanate methyl benzene or 4,4'-diphenylmethane diisocyanate; a (meth)acrylate monomer compound which has an aromatic ring and an ether linkage such as 2,2-bis(meth)acryloxyphenyl)propane, 2,2-bis(4-(3-meth)acryloxy)-2-hydroxypropoxyphenyl)propane, 2,2-bis(4-(meth)acryloxyethoxyphenyl)propane, 2,2-bis(4-(meth)acryloxydiethoxyphenyl)propane, 2,2-bis(4-(meth)acryloxytetraethoxyphenyl)propane, 2,2-bis(4-(meth)acryloxypentaethoxyphenyl)propane, 2,2-bis(4-(meth)acryloxypolyethoxyphenyl)propane, 2,2-bis(4-(meth)acryloxydiprop ooxyphenyl)propane, 2-(4-(meth)acryloxyethoxyphenyl)-2-(4-(meth)acryloxy phenyl) propane, 2-(4-(meth)acryloxydiethoxyphenyl)-2-(4-(meth)acryloxytriethoxyphenyl)propane, 2-(4-(meth)acryloxydipropoxyphenyl)-2-(4-(meth)acryloxytriethoxyphenyl)propane and 2,2-bis(4-(meth)acryloxyisopropoxyphenyl)propane, a reactant of 1:2 ratio of bisphenol A or hydrogenated bisphenol A to glycidyl (meth)acrylate, e.g., an adduct of 1:2 ratio of a bisphenol A or hydrogenated bisphenol A to an epoxy group-containing (meth)acrylate such as a bisphenol A diglycidyl ether(meth) acrylic acid adduct.

Specific examples of the radical polymerizable monomer compound may be multifunctional monomer compounds which have three or more polymerizable functional groups including trimethylolmethane tri(meth)acrylate, trimethylolethane tri(meth)acrylate, trimethylolpropane tri(meth)acrylate, pentaerythritol tetra(meth)acrylate, phosphazene-based tri(meth)acrylate, isocyanuric acid-based tri(meth)acrylate, pentaerythritol tetra(meth)acrylate, and ditrimethylolpropane tetra(meth)acrylate, and urethane-based monomer compound which is derived from a vinyl monomer having a hydroxy group such as glycidol di(meth)acrylate, and a diisocyanate compound such as diisocyanate methylbenzene, 4,4'-diphenylmethane diisocyanate, hexamethylene diisocyanate, trimethylhexamethylene diisocyanate, diisocyanate methylcyclohexane, isophorone diisocyanate and methyl bis(4-cyclohexylisocyanate), monomer compound having five or more ethylenically unsaturated groups such as dipentaerythritol hydroxypenta(meth)acrylate, polymerizable multifunctional acrylate having polyethylenically unsaturated carbamoylisocyanurate; urethane bond-containing polymerizable multifunctional acrylate such as phenylglycidyl ether acrylate hexamethyllene diisocianate urethane prepolymer, phenylglycidyl ether toluene diisocyanate urethane prepolymer, pentaerythritol triacrylate toluene diisocyanate urethane prepolymer and pentaerythritol triacrylate isophorone diisocyanate urethane prepolymer; ditrimethylolpropane tetraacrylate, ethoxylated pentaerythritol tetraacrylate, propoxylated pentaerythritol tetraacrylate, pentaerythritol tetra(meth)acrylate, dipentaerythritol tetra (meth)acrylate, dipentaerythritol penta(meth)acrylate, dipentaerythritol hexa(meth)acrylate and trimethylpropane tri(meth)acrylate.

In the present invention, a relationship between a refractive index of a curable resin obtained by polymerizing and curing a radical polymerizable monomer compound and a refractive index of a fiber material is important for adjusting a transparency of each layer of a composite material. Namely, when a difference between a refractive index of a curable resin obtained by polymerizing and curing a radical polymerizable monomer compound and a refractive index of a fiber material is large, a transparency of a composited material becomes low. On the other hand, when the difference is small, a transparency of a composited material becomes high. In the present invention, a curable resin may be obtained by polymerizing and curing a single radical polymerizable monomer compound. However, when a curable resin is obtained by polymerizing and curing a plurality of radical polymerizable monomer compounds having different refractive indexes, there are advantages that a refractive index can be controlled, thereby becoming easily designable a transparency of a composite material.

Known Catalysts may be used, without any limitation, for a polymerization catalyst compound used in polymerizing and curing a radical polymerizable monomer compound constituting a curable resin. Examples of a photopolymerization catalyst include benzophenone, diacetyl, benzil, 4,4'-dimethoxybenzil, 4,4'-oxybenzil, 4,4'-chlorobenzil, camphorquinone, camphorquinonecarboxylic acid, 2,3-pentadione, 2,3-octadione, 9,10-phenanthrenequinone, acenaphthenequinone, 2,4,6-trimethylbenzoyldiphenylphosphine oxide, 2,6-dimethylbenzoyldiphenylphosphine oxide, 2,6-dimethoxybenzoyldiphenylphosphine oxide, 2,6-dichlorobenzoyldiphenylphosphine oxide, 2,3,5,6-tetramethylbenzoyldiphenylphosphine oxide, 2,4,6-trimethylbenzoylphenyl phosphinic methyl, 2,4,6-trimethylbenzoylphenyl phosphinic ethylester, and 2,4,6-trimethylbenzoylphenyl phosphinic phenylester. Examples of useful thermal (chemical) polymerization catalyst compound include diacyl peroxides, peroxy esters, dialkyl peroxides, peroxy ketals, ketone peroxides and hydroperoxides. In particular, examples of diacyl peroxides include benzoyl peroxide, 2,4-dichlorobenzoyl peroxide, and m-toluoyl peroxide.

In some embodiments, a reducing agent may be added as a polymerization catalyst compound. Reducing agents known in the art may be used, without any limitation. Examples of the reducing agent include N,N-dimethylaniline, N,N-diethylaniline, N,N-dibenzylaniline, N,N-dimethyl-p-toluidine, N,N-diethyl-p-toluidine, N,N-dihydroxyethyl-p-toluidine, N,N-dimethylbenzoic acid, N,N-diethylbenzoic acid, N,N-dimethylbenzoic acid ethyl, N,N-diethylbenzoic acid ethyl, N,N-dimethylbenzoic acid methyl, N,N-diethylbenzoic acid methyl, N,N-dimethylaminobenzaldehyde, N,N-dihydroxyethylaniline, p-dimethylamino phenethyl alcohol, N,N-dimethylaminoethyl methacrylate, triethylamine, tributylamine, tripropylamine, and N-ethylethanolamine.

The above described polymerization catalyst compounds may be added singly or in combinations. The content of polymerization catalyst compound is preferably 0.01 to 5 parts by weight, more preferably 0.05 to 3 parts by weight, and still more preferably 0.1 to 2 parts by weight based on 100 parts by weight of a radical polymerizable monomer. If the content of the polymerization catalyst compound is too small, sufficient polymerization of a radical polymerizable monomer compound is not achieved. On the other hand, if the content of the polymerization catalyst compound is too large, it causes lowering of a strength of a composite material as a result of promoting termination reactions during polymerization.

In the preparation of a block-like composite material according to the present invention, a chain transfer agent was added to a radical polymerizable monomer, thereby enabling uniform polymerization and curing. For a chain transfer agent, a known compound can be used without any limitation. Specific examples include mercaptan compounds such as n-butylmercaptan and n-octylmercaptan, terpenoid compounds such as limonene, myrcene, α-terpinene, β-terpinene, γ-terpinene, terpinolene, β-pinene and α-pinene, and α-methylstyrene dimer. Among these chain transfer materials, terpenoid compounds are particularly preferable. Specifically, α-terpinene, β-terpinene, γ-terpinene are particularly preferable. The content of such a chain transfer agent is preferably 0.001 to 1 part by weight, particularly preferably 0.1 parts by weight or more and 0.5 parts by weight or less based on 100 parts by weight of the radical polymerizable monomer compound.

For a fiber material to be incorporated in a block-like composite material of the present invention, a known fiber material used for a dental material may be use without any limitation. For a shape of a fiber material, various bundle (knit) shapes including roving consisting of collected single fibers having a diameter of 1 to 100 μm, strand, yarn, sheet (cloth), ribbon, and tape, and irregular shapes such as glass wool may be used without any limitation. In the case of the purpose of using for a bridge to restore a loss tooth, the shape of a fiber material is preferably roving, yarn, sheet (cloth), ribbon, and tape of a long-fiber material from the view point of strength. In preparation of a composite material of the present invention, the shape of a fiber material is preferably sheet from the view point of easiness in layering.

As to the quality of the material of a fiber material, glass fiber such as A-glass, C-glass, D-glass, E-glass, ECR-glass, AR-glass, R-glass, S-glass, etc., ceramics fiber such as alumina, zirconia, etc., resin fiber such as polyethylene, polyester, polyamide, etc., and collagen fiber from the view point of biocompatibility may be used without any limitation.

The content of a fiber material is preferably 10 to 90 wt %, more preferably 20 to 80 wt %, and still more preferably 30 to 70 wt % in a block-like composite material of the present invention. If the content of a fiber material is too small, a composite material does not have sufficient strength. In addition, it becomes difficult to uniformly compound a fiber material in a molded product. On the other hand, if the content of a fiber material is too large, it brings a problem in molding into a block-like shape because of difficulty in compositing with a curable resin.

In order to increase the hardness and compressive strength of a block-like composite material of the present invention, it is effective that a filler other than a fiber material is added. Examples of a filler which can be suitably used include kaolin, talc, quartz, silica, colloidal silica, alumina, aluminosilicate, silicon nitride, barium sulfate, calcium phosphate, glass powder, fluoroaluminosilicate glass, zirconia, zirconium silicate etc. Shape, grain size distribution, and average particle diameter of a filler are not limited especially. However, because a filler is combined with a fiber material during filling of a filler, it is preferable that average particle diameter is 50 µm or less, preferably 10 µm or less, more preferably 1 µm or less. The content of a filler other than a fiber material is 1 to 50 wt %, preferably 3 to 30 wt %, and more preferably 5 to 20 wt % in a block-like composite material of the present invention. The content of a filler correlates to the content of a fiber material, but if the content of the filler is too large, the elastic modulus of the composite material becomes too large, leading to a decrease in resilience which is a characteristic of the composite material containing the fiber material.

A fiber material and a filler to be used in a block-like composite material according to the present invention are preferably applied with surface treatment. Examples of a surface treatment agent for inorganic fillers include silane compounds, such as vinyltrimethoxysilane, vinyltriethoxysilane, vinyltrichlorosilane, vinyltri(β-methoxyethoxy)silane, γ-methacryloxypropyltrimethoxysilane, γ-glycidoxypropyltrimethoxysilane, γ-mercaptopropyltrimethoxysilane, and γ-aminopropyltriethoxysilane. In the case of using an organic fiber material, plasma processing etc., may be used.

A block-like composite material having a multilayered structure including at least two layers having different transparencies of the present invention may include a colorant material and/or a masking material to adjust the transparency of each layer. Colorant materials and/or masking materials which are commonly used for a dental material may be used without any limitation. From the view point of masking effect, color tone stability, and biocompatibility, titanium oxide may be used suitably.

In order to impart a color tone similar to a natural tooth in addition to a transparency similar to a natural tooth, a block-like composite material of the present invention may contain a colorant material and/or a fluorescent material. When a colorant material is added, the content preferably varies between a low transparent portion on the assumption of a dentin and a highly transparent portion on the assumption of an enamel. Further, various additives such as a polymerization inhibitor and/or an ultraviolet absorbing agent may be added to a composite material of the present invention, if desired.

A block-like composite material of the present invention can have a layered structure including layers having different transparencies by adjusting a difference in refractive index between the curable resin and the fiber material. Specifically, a portion containing a fiber material having a refractive index approximate to that of the curable resin has a high transparency, while a portion containing a fiber material having a refractive index significantly different from that of the curable resin has a low transparency.

In some embodiments where a block-like composite material includes two layers, it is possible to reproduce a dentine and an enamel by setting a contrast ratio of a highly transparent layer to less than 0.55 and setting a contrast ratio of the low transparent layer to 0.55 or more.

In some embodiments where a block-like composite material includes three layers, a contrast ratio of a highly transparent layer is set to less than 0.50, a contrast ratio of the middle transparency layer is set to 0.50 or more and less than 0.60, and a contrast ratio of the low transparent layer is set to 0.60 or more. By including the middle transparency layer, a transparency of a block-like composite material varies transiently, therefore a color tone of the natural teeth may be reproduced with natural feeling.

In some embodiments where the block-like composite material includes four or more layers, a contrast ration of a highly transparent layer is set to less than 0.50, a contrast ratio of the middle transparency layer is set to 0.50 or more and less than 0.60, a contrast ratio of the low transparent layer is set to 0.60 or more, each of the highly transparent layer, the middle transparency layer and the low transparent layer consists of a single layer or a plurality of layers having different transparencies, and a difference of contrast ratio between each layers is 0.02 or more. By increasing the number of layers having different transparencies, a transparency of a block-like composite material varies more transiently, therefore a color tone of a natural tooth may be reproduced with more natural feeling.

Although a method for preparing a block-like composite material of the present invention is not limited especially, following methods are considered as examples. A mold having a desired shape is prepared, and a first fiber material is set in the mold. A second fiber material having a refractive index different from that of the first fiber material is set on the first fiber material, and a radical polymerizable monomer compound is poured into the mold, intimately contacted with the fiber materials, and then polymerized and cured.

In another method, a first fiber material is set in a mold having a desired shape, and a first radical polymerizable monomer compound is poured in only the portion where the first fiber material is set. A second fiber material is set on this layer in the mold, and a second radical polymerizable monomer compound is poured in the portion where the second fiber material is set. In this method, polymerizing and curing may be allowed to proceed for each layer or may be allowed to proceed for all layers by once time.

When the longer axis of a fiber material is short (equal to or less than 1 cm), a fiber material may be made into a paste by blending with a radical polymerizable monomer compound in advance. In this paste process, pastes containing respective fiber materials with different refractive indexes are provided and filled in the mold in order, and then polymerized and cured.

In the case of adjusting a transparency of each layer by a colorant material and/or a masking material, a colorant material and/or a masking material are mixed sufficiently with a radical polymerizable monomer compound to prepare a mixture, and the mixture is poured in the mold in which a fiber material has been set. By varying the content of a colorant material and/or a masking material, it becomes possible to impart each layer of a layered structure with different transparencies.

A shape of a block-like composite material for dental cutting and processing of the present invention is not limited especially. A rectangular parallelepiped shape and a disk shape may be processed by a common dental CAD/CAM system. By approximating a shape of a mold used in preparation to a crown shape, a composite material having approximately crown shape may be obtained to reduce time and labor of cutting and processing. In this case, the shape of each layer is preferably designed into a curved shape corresponding to a crown shape.

EXAMPLES

Hereinafter, Examples of the present invention are specifically described. However, the present invention is not intended to be limited to these Examples.

Mixed liquid A of radical polymerizable monomer compounds was prepared by compounding 50 parts by weight of 2,2-bis[4-(3-methacryloxy)-2-hydroxypropoxyphenyl]propane (Bis-GMA), 50 parts by weight of triethylene glycol dimethacrylate (3G), and 0.3 parts by weight of benzoyl peroxide (BPO). The refractive index of a curable resin obtained by polymerizing and curing mixed liquid A of radical polymerizable monomer compounds was 1.535.

Mixed liquid B of radical polymerizable monomer compounds was prepared by compounding 70 parts by weight of 1,6-bismethacrylethylcarbonylamino(2,2,4-)trimethyl-hexane (UDMA), 30 parts by weight of triethylene glycol dimethacrylate (3G), and 0.3 parts by weight of benzoyl peroxide (BPO). The refractive index of a curable resin obtained by polymerizing and curing mixed liquid B of radical polymerizable monomer compounds was 1.505.

Mixed liquid C of radical polymerizable monomer compounds was prepared by compounding 70 parts by weight of 2,2-bis[4-(3-methacryloxy)-2-hydroxypropoxyphenyl]propane (Bis-GMA), 30 parts by weight of triethylene glycol dimethacrylate (3G), and 0.3 parts by weight of benzoyl peroxide (BPO). The refractive index of a curable resin obtained by polymerizing and curing mixed liquid C of radical polymerizable monomer compounds was 1.553.

[Preliminary Test]

E-glass fibers (refractive index: 1.558) were laid in a rectangular parallelepiped shape mold of 12×14×18 mm to a height of 1 mm. Mixed liquid A of radical polymerizable monomer compounds was poured in gaps between the E-glass fibers. Then, the content of the mixed liquid A of radical polymerizable monomer compounds was adjusted so that the content of the fiber material was 55 wt % and the content of mixed liquid A of radical polymerizable monomer compounds was 45 wt %. The mold was heated to 100° C. to allow thermal polymerization to proceed, thereby obtaining a plate-like composite material. The colorimetric value was measured on a white background, and the colorimetric value was measured on a black background for this composite material having a thickness of 1 mm by a spectral colorimeter. A contrast ratio was obtained by dividing the value Y measured on a black background, by the value Y measured on a white background. The same test was performed for respective composite materials containing different combinations of a fiber material and a mixed liquid of radical polymerizable monomer compounds to obtain the contrast ratio of each combination. The results are shown in Tables 1-1, and 1-2.

Example 1

E-glass fibers (refractive index: 1.558) were laid in a rectangular parallelepiped shape mold of 12×14×18 mm to a height of 6 mm. S-glass fibers (refractive index: 1.521) were laid on the E-glass fibers in the mold to a height of 6 mm. Mixed liquid A of radical polymerizable monomer compounds was poured in gaps between the E-glass fibers and in gaps between the S-glass fibers. Then, the content of mixed liquid A of radical polymerizable monomer compounds was adjusted so that the total content of the two kinds of fiber materials was 55 wt % and the content of mixed liquid A of radical polymerizable monomer compounds was 45 wt %. The mold was heated to 100° C. to allow thermal polymerization to proceed, thereby obtaining a block-like composite material including two kinds of fiber materials. In this block-like composite material, the transparency of each layer which are located with one fiber material among two different kinds of fiber materials, are different each other. An opacity of a layer (contrast ratio: 0.58) located with the E-glass fiber was higher than that of a layer (contrast ratio: 0.46) located with the S-glass fiber.

Examples 2, 3

Block-like composite materials containing different combinations of a fiber material and a mixed liquid of radical polymerizable monomer compounds were prepared by the same method as in Example 1. The fiber materials and mixed liquids of radical polymerizable monomer compounds used in these Examples are shown in Table. A block-like composite material including two layers having different transparencies were obtained in both Examples 2 and 3.

Examples 4, 5

Block-like composite materials containing different combinations of a fiber material and a mixed liquid of radical polymerizable monomer compounds were prepared by the same method as in Example 1. The fiber materials and mixed liquids of radical polymerizable monomer compounds used in these Examples are shown in Table. In Example 4, the layers containing different fiber materials had a high transparency, and a low contrast of transparency between the layers. In Example 5, the layers containing different fiber materials had a low transparency, and a low contrast of transparency between the layers.

Example 6

ECR-glass fibers (refractive index: 1.570) were laid in a rectangular parallelepiped shape mold of 12×14×18 mm to a height of 4 mm. E-glass fibers (refractive index: 1.558) were laid on the ECR-glass fibers in the mold to a height of 4 mm and S-glass fibers (refractive index: 1.521) were laid on the E-glass fibers in the mold to a height of 4 mm. Mixed liquid A of radical polymerizable monomer compounds was poured in gaps between the ECR-glass fibers, in gaps between the E-glass fibers, and in gaps between the S-glass fibers. Then, the content of mixed liquid A of radical polymerizable monomer compounds was adjusted so that the total content of the three kinds of fiber materials was 55 wt % and the content of mixed liquid A of radical polymerizable monomer compounds was 45 wt %. The mold was heated to 100° C. to allow thermal polymerization to proceed, thereby obtaining a block-like composite material including three kinds of fiber materials. A transparency of this block-like composite material varied in three steps.

Example 7

ECR-glass fibers (refractive index: 1.570) were laid in a rectangular parallelepiped shape mold of 12×14×18 mm to a height of 4 mm. AR-glass fibers (refractive index: 1.562) were laid on the ECR-glass fibers in the mold to a height of 2 mm, E-glass fibers (refractive index: 1.558) were laid on the AR-glass fibers in the mold to a height of 2 mm and S-glass fibers (refractive index: 1.521) were laid on the E-glass fibers in the mold to a height of 4 mm. Mixed liquid A of radical polymerizable monomer compounds was poured in gaps between the ECR-glass fibers, in gaps between the AR-glass fibers, in gaps between the E-glass fibers, and in gaps between the S-glass fibers. The content of mixed liquid A of radical polymerizable monomer compounds was adjusted so that the total content of the four kinds of fiber materials was 55 wt % and the content of mixed liquid A of radical polymerizable monomer compounds was 45 wt %. The mold was heated to 100° C. to allow thermal polymerization to proceed, thereby obtaining a block-like composite material including four kinds of fiber materials. A transparency of this block-like composite material varied in four steps.

Example 8

ECR-glass fibers (refractive index: 1.558) were laid in a rectangular parallelepiped shape mold of 12×14×18 mm to a height of 6 mm. Mixed liquid A of radical polymerizable monomer compounds was poured to the same height as that of laid ECR-glass fibers. Then, in a range to 6 mm, the content of mixed liquid A of radical polymerizable monomer compounds was adjusted so that the content of the ECR-glass fibers was 55 wt % and the content of mixed liquid A of radical polymerizable monomer compounds was 45 wt %. AR-glass fibers (refractive index: 1.562) were laid on this layer in the mold to a height of 6 mm. Mixed liquid C of radical polymerizable monomer compounds was poured in the layer in which the AR-glass fibers were laid. Then, in a range to 6 mm, the content of mixed liquid C of radical polymerizable monomer compounds was adjusted so that the content of the AR-glass fiber was 55 wt % and the content of mixed liquid C of radical polymerizable monomer compounds was 45 wt %. The mold was heated to 100° C. to allow thermal polymerization to proceed, thereby obtaining a block-like composite material. In this block-like composite material, an opacity of a layer (contrast ratio: 0.70) located with the ECR-glass fibers and poured with mixed liquid A of radical polymerizable monomer compounds was higher than that of a layer (contrast ratio: 0.38) located with the AR-glass fibers and poured with mixed liquid C of radical polymerizable monomer compounds.

Example 9

To mixed liquid C of radical polymerizable monomer compounds was added 0.08 wt % of titanium oxide and the titanium oxide was dispersed sufficiently by a mortar to prepare mixed liquid C2 of radical polymerizable monomer compounds. To mixed liquid C of radical polymerizable monomer compounds was added 0.02 wt % of titanium oxide and the titanium oxide was dispersed sufficiently by a mortar to prepare mixed liquid C3 of radical polymerizable monomer compounds. E-glass fibers (refractive index: 1.558) were laid in a rectangular parallelepiped shape mold of 12×14×18 mm to a height of 6 mm. Mixed liquid C2 of radical polymerizable monomer compounds was poured in gaps between the E-glass fibers. Then, in a range to 6 mm, the content of mixed liquid C2 of radical polymerizable monomer compounds was adjusted so that the content of the E-glass fiber was 55 wt % and the content of mixed liquid C2 of radical polymerizable monomer compounds was 45 wt %. E-glass fibers were laid on this layer in the mold to a height of 6 mm. Mixed liquid C3 of radical polymerizable monomer compounds was poured in gaps between the E-glass fibers. Then, in a range to 6 mm, the content of mixed liquid C3 of radical polymerizable monomer compounds was adjusted so that the content of the E-glass fibers was 55 wt % and the content of mixed liquid C3 of radical polymerizable monomer compounds was 45 wt %. The mold was heated to 100° C. to allow thermal polymerization to proceed, thereby obtaining a block-like composite material. This block-like composite material includes two layers having different transparencies. It was confirmed that a contrast ratio of the layer of mixed liquid C2 of radical polymerizable monomer compounds and the E-glass fiber was 0.69, and a contrast ratio of the layer of mixed liquid C3 of radical polymerizable monomer compounds and the E-glass fiber was 0.47, by a preliminary test.

TABLE 1

| | Preliminary test 1 | Preliminary test 2 | Preliminary test 3 | Preliminary test 4 | Preliminary test 5 |
| --- | --- | --- | --- | --- | --- |
| Mixed liquid of radical polymerizable monomer compounds | Mixed liquid A of radical polymerizable monomer compounds (Refractive index: 1.535) | Mixed liquid A of radical polymerizable monomer compounds (Refractive index: 1.535) | Mixed liquid B of radical polymerizable monomer compounds (Refractive index: 1.505) | Mixed liquid B of radical polymerizable monomer compounds (Refractive index: 1.505) | Mixed liquid A of radical polymerizable monomer compounds (Refractive index: 1.535) |
| Fiber material | E-glass fiber (Refractive index: 1.558) | S-glass fiber (Refractive index: 1.521) | E-glass fiber (Refractive index: 1.558) | S-glass fiber (Refractive index: 1.521) | ECR-glass fiber (Refractive index: 1.570) |
| Contrast ratio | 0.58 | 0.46 | 0.79 | 0.49 | 0.70 |

| | Preliminary test 6 | Preliminary test 7 | Preliminary test 8 | Preliminary test 9 | Preliminary test 10 |
| --- | --- | --- | --- | --- | --- |
| Mixed liquid of radical polymerizable monomer compounds | Mixed liquid C of radical polymerizable monomer compounds (Refractive index: 1.553) | Mixed liquid C of radical polymerizable monomer compounds (Refractive index: 1.553) | Mixed liquid C of radical polymerizable monomer compounds (Refractive index: 1.505) | Mixed liquid B of radical polymerizable monomer compounds (Refractive index: 1.505) | Mixed liquid A of radical polymerizable monomer compounds (Refractive index: 1.535) |

TABLE 1-continued

| Fiber material | E-glass fiber (Refractive index: 1.558) | AR-glass fiber (Refractive index: 1.562) | AR-glass fiber (Refractive index: 1.562) | ECR-glass fiber (Refractive index: 1.570) | AR-glass fiber (Refractive index: 1.562) |
|---|---|---|---|---|---|
| Contrast ratio | 0.31 | 0.38 | 0.80 | 0.89 | 0.62 |

TABLE 2

|  | Example 1 | Example 2 | Example 3 |
|---|---|---|---|
| First layer | Mixed liquid A of radical polymerizable monomer compounds and E-glass fiber Contrast ratio: 0.58 | Mixed liquid B of radical polymerizable monomer compounds and E-glass fiber Contrast ratio: 0.79 | Mixed liquid A of radical polymerizable monomer compounds and ECR-glass fiber Contrast ratio: 0.70 |
| Second layer | Mixed liquid A of radical polymerizable monomer compounds and S-glass fiber Contrast ratio: 0.46 | Mixed liquid B of radical polymerizable monomer compounds and S-glass fiber Contrast ratio: 0.49 | Mixed liquid A of radical polymerizable monomer compounds and S-glass fiber Contrast ratio: 0.46 |

|  | Example 4 | Example 5 | Example 6 |
|---|---|---|---|
| First layer | Mixed liquid C of radical polymerizable monomer compounds and E-glass fiber Contrast ratio: 0.31 | Mixed liquid B of radical polymerizable monomer compounds and AR-glass fiber Contrast ratio: 0.80 | Mixed liquid A of radical polymerizable monomer compounds and ECR-glass fiber Contrast ratio: 0.70 |
| Second layer | Mixed liquid C of radical polymerizable monomer compounds and AR-glass fiber Contrast ratio: 0.38 | Mixed liquid B of radical polymerizable monomer compounds and ECR-glass fiber Contrast ratio: 0.89 | Mixed liquid A of radical polymerizable monomer compounds and E-glass fiber Contrast ratio: 0.58 |
| Third layer | — | — | Mixed liquid A of radical polymerizable monomer compounds and S-glass fiber Contrast ratio: 0.46 |

|  | Example 7 | Example 8 | Example 9 |
|---|---|---|---|
| First layer | Mixed liquid A of radical polymerizable monomer compounds and ECR-glass fiber Contrast ratio: 0.70 | Mixed liquid A of radical polymerizable monomer compounds and ECR-glass fiber Contrast ratio: 0.70 | Mixed liquid C2 of radical polymerizable monomer compounds and E-glass fiber Contrast ratio: 0.69 |
| Second layer | Mixed liquid A of radical polymerizable monomer compounds and AR-glass fiber Contrast ratio: 0.62 | Mixed liquid C of radical polymerizable monomer compounds and AR-glass fiber Contrast ratio: 0.38 | Mixed liquid C3 of radical polymerizable monomer compounds and E-glass fiber Contrast ratio: 0.47 |
| Third layer | Mixed liquid A of radical polymerizable monomer compounds and E-glass fiber Contrast ratio: 0.58 | — | — |
| Forth layer | Mixed liquid A of radical polymerizable monomer compounds and S-glass fiber Contrast ratio: 0.46 | — | — |

INDUSTRIAL APPLICABILITY

A block-like composite material for dental cutting and processing of the present invention may be cut and processed by a dental CAD/CAM system, and may provide a dental prosthesis device (crown, bridge) having both high strength and high esthetics.

What is claimed is:

1. A block-like composite material for dental cutting and processing, wherein
the block-like composite material has a multilayered structure comprising at least two layers having different transparencies including a highly transparent layer and a low transparent layer,
wherein:
the each layer includes a curable resin and a fiber material,
the different transparencies are obtained by adjusting a difference in refractive indexes between the curable resin and the fiber material in each of the at least two layers,
the highly transparent layer has a higher transparency than the low transparent layer, and
a boundary between the layers consists of a flat plane.

2. The block-like composite material for dental cutting and processing according to claim 1, wherein,
the block-like composite material includes three layers consisting of the highly transparent layer, a middle transparency layer and the low transparent layer,
a contrast ratio of the highly transparent layer is less than 0.50,
a contrast ratio of the middle transparency layer is 0.50 or more and less than 0.60, and
a contrast ratio of the low transparent layer is 0.60 or more.

3. The block-like composite material for dental cutting and processing according to claim 1, wherein,
the block-like composite material includes four or more layers comprising the highly transparent layer, a middle transparency layer and the low transparent layer,
a contrast ratio of the highly transparent layer is less than 0.50,
a contrast ratio of the middle transparency layer is 0.50 or more and less than 0.60,
a contrast ratio of the low transparent layer is 0.60 or more,
each of the highly transparent layer, the middle transparency layer and the low transparent layer consists of a single layer or a plurality of layers having different transparencies, and
a difference of contrast ratio between each layer is 0.02 or more.

4. The block-like composite material for dental cutting and processing according to claim 1, wherein,
a shape of the fiber material is at least one selected from the group consisting of roving, strand, yarn, sheet, ribbon, and tape.

5. The block-like composite material for dental cutting and processing according to claim 4, wherein,
the fiber material is formed from a long-fiber material.

6. The block-like composite material for dental cutting and processing according to claim 4, wherein,
the fiber material is formed from at least one selected from the group consisting of A-glass, C-glass, D-glass, E-glass, ECR-glass, AR-glass, R-glass, S-glass, alumina, zirconia, polyethylene, polyester, polyamide, and collagen.

7. The block-like composite material for dental cutting and processing according to claim 1, wherein,
refractive indexes of the curable resins in the respective layers are the same as each other.

8. The block-like composite material for dental cutting and processing according to claim 1, wherein,
a contrast ratio of the highly transparent layer is less than 0.50, and
a contrast ratio of the low transparent layer is 0.50 or more.

9. The block-like composite material for dental cutting and processing according to claim 1, wherein,
a content of the fiber material is from 30 to 70 wt % of the block-like composite material, and
a content of a filler other than the fiber material is 50 wt % or less of the block-like composite material.

* * * * *